United States Patent
Gerhard et al.

(10) Patent No.: US 6,891,980 B2
(45) Date of Patent: May 10, 2005

(54) METHOD AND APPARATUS FOR ANALYSIS OF SCHLIEREN

(75) Inventors: Michael Gerhard, Aalen (DE); Frank-Thomas Lentes, Bingen (DE); Christian Kusch, Jena (DE); Wolfgang Singer, Aalen (DE); Ewald Moersen, Mainz (DE)

(73) Assignees: Schott Glas, Mainz (DE); Carl Zeiss SMT AG, Oberkochen (DE)

( * ) Notice: Subject to any disclaimer, the term of this patent is extended or adjusted under 35 U.S.C. 154(b) by 608 days.

(21) Appl. No.: 10/090,975
(22) Filed: Mar. 5, 2002
(65) Prior Publication Data

US 2002/0154814 A1 Oct. 24, 2002

(30) Foreign Application Priority Data

Mar. 9, 2001 (DE) .......................................... 101 11 450

(51) Int. Cl.[7] ................................................ G06K 7/10
(52) U.S. Cl. ...................................... 382/321; 382/312
(58) Field of Search .............................. 382/141, 312, 382/321; 315/383, 382; 348/744, 810; 356/129, 237.2; 313/452, 453

(56) References Cited

U.S. PATENT DOCUMENTS

| | | | | |
|---|---|---|---|---|
| 4,121,247 A | | 10/1978 | Henry | 348/135 |
| 5,291,102 A | * | 3/1994 | Washburn | 315/383 |
| 5,399,947 A | * | 3/1995 | Washburn | 315/383 |
| 5,583,632 A | * | 12/1996 | Haga | 356/129 |
| 5,585,691 A | * | 12/1996 | Washburn | 313/452 |
| 5,694,479 A | | 12/1997 | Guering et al. | 382/141 |
| 5,764,345 A | | 6/1998 | Fladd et al. | 356/35.5 |
| 5,988,645 A | * | 11/1999 | Downing | 273/348 |

FOREIGN PATENT DOCUMENTS

| | | | | | |
|---|---|---|---|---|---|
| JP | 405181166 A | * | 7/1993 | | G02F/1/137 |
| WO | WO009102429 | * | 2/1991 | | G09F/9/30 |

* cited by examiner

*Primary Examiner*—Anh Hong Do
(74) *Attorney, Agent, or Firm*—Michael J. Striker

(57) ABSTRACT

The method for evaluating schlieren in glassy or crystalline optical materials includes irradiating a test sample of the optical material with light and producing a shadow image of the test sample on a projection screen. The shadow image of the test sample is received in an electronic image receiving device, such as a digital camera, and is compared with another shadow image of schlieren obtained with a comparison sample by means of interferometry. Then the optical material of the test sample is evaluated with the help of the comparison results.

16 Claims, 3 Drawing Sheets

METHOD AND APPARATUS FOR ANALYSIS OF SCHLIEREN

BACKGROUND OF THE INVENTION

1. Field of the Invention

The present invention relates to a method and apparatus for evaluation of schlieren in optical materials by means of shadow methods.

2. Description of the Related Art

Schlieren, according to conventional speech usage, are bounded regions in optical materials, which act optically because of local changes in refractive index and are mostly visible in an image or picture in the form of filaments, strips and bands. Nearly all optical materials do not have an index of refraction that is exactly constant throughout, but instead it varies within a certain range. Schlieren are defined as optical inhomogeneities of small structural width and a high refractive index gradient.

A variety of different methods are known for detection of schlieren in optical materials. Practically all these methods are based on detecting changes of the optical wave front after passing through the sample to be tested and analyzed. Interferometry, Töpler methods and shadow methods are the most widely used methods.

Changes in the wave front are detected directly by means of interferometry and Töpler methods; however surface imperfections and faults on the test sample, such as surfaces that are not completely planar, effect the measurement directly. These measurements involve great effort and expense because of the high requirements for surface uniformity of the test sample.

Usually commercially obtained interferometers are not ready for schlieren measurements; i.e. if schlieren must be measured with an interferometer, it must be constructed for that purpose. Thus it is important that spatial resolution of the interferometer is sufficient so that fine schlieren structures can be detected, whose size is in the micron range.

To detect schlieren it is preferably to use shadow methods, because they are comparatively sensitive and can be performed when the surface quality of the samples is similar to that of typical optical materials.

In shadow methods the optical material is either between a light source and the eye of an observer and the shadow casting schlierens are established by moving and tilting the sample (MIL-G-174A and similar standards), or the sample is irradiated with light and the schlieren contained in the sample are projected as shadows (DDR Professional Standard TGL 21790, similar ISO standard is widely distributed).

Also DIN 3140, Part 3, concerns schlieren, however in practice has only a limited significance.

Since schlieren are spatial formations, the methods described in Standard TGL 21790 and also in DIN 3140 attempt to characterize the extent of the schlieren by an effective schlieren surface or area. Known procedures have the disadvantage that they depend strongly on the subjective evaluation of the observer. In Standard TGL 21790 definite schlieren comparisons are derived from measurement of visibility threshold. However the comparison of the schlieren image with a test pattern occurs in the known methods only by eye and thus depends on the subjective observation powers of the observer to some extent.

In the conventional procedure the shadow image of the respective test sample is copied onto a piece of paper, the width and the intensity of the individual shadow lines is subjectively evaluated and the evaluation or analysis is registered on the sketch.

Furthermore the above-described standard is exclusively related to glass and glass-like substances. However increasingly crystalline materials are used for optical components, especially for wavelengths, which are outside of the visible range, which means substantially below about 400 nm and above about 800 nm. Thus, for example, there is an increasing demand for monocrystalline materials made of alkali and alkaline earth fluorides ($CaF_2$, $BaF_2$, $SrF_2$, among others) for UV applications, such as UV lithography or lenses and widows for irradiation and imaging apparatuses. Crystals provide the basis for many optical elements in the IR spectral range.

Glasses and crystals differ by their respective disorderly and orderly structures. Schlieren in crystals can have entirely different causes than schlieren in glass. The activity of schlieren in crystals depends, among other things, very strongly on the position and orientation of the inhomogeneities producing the schlieren (e.g. grain boundaries). In crystals schlieren can be produced by band-shaped structures of greater width, but of only reduced thickness (e.g. displacements, small angle grain boundaries). The methods developed for glasses are not suitable to analyze substrates with schlieren of this type permeating them with the required accuracy.

Also the test or comparison schlieren samples used for glasses are not usable for crystals because of the completely different mechanisms for producing schlieren in crystals. A coating in the known comparative schlieren test plate developed for testing optical glass simulates phase discontinuities of different thicknesses and widths. However one such two-dimensional schlieren test plate is not suitable for representing the action of schlieren in crystals.

Especially during testing for the present invention the phase deviation or shift has the opposite sign in single crystalline materials from that in glasses. The schlieren test and comparison plate known up to now however usually is made from an insensitive material, for example quartz or quartz glass. Different structures are provided in this plate, e.g. by means of a thin coating and a photo mask. Usually cavities or openings of e.g. 0.2 mm width and 1 cm length are provided in a 10 nm coating, whereby a phase shift is produced when a wave front passes through. In principle, it is also possible to produce a phase shift by application of raised regions instead of cavities or openings, whereby the sign of the shift changes. The subjective intensity and width of the lines in the shadow image evaluated with the help of the comparison or test plate however has no reliable significance for test samples made from crystalline material, since a change of the light wave front is caused by a change in the index of refraction. It has been found in the scope of the invention that the results obtained by comparison with known schlieren test plates with the shadow methods for crystals are mostly unusable and unreliable. In practice they produce no relevant conclusions regarding the quality of the crystalline optical elements.

SUMMARY OF THE INVENTION

It is an object of the present invention to provide a method and an apparatus for objective analysis and evaluation of schlieren by means of shadow methods, which is suitable not only for optical glass materials but also for crystalline materials.

Furthermore it is another object of the present invention to provide a method, which is independent of the currently used subjective methods for analysis and evaluation of schlieren by means of shadow methods.

It is also an object of the present invention to provide an apparatus for performing these methods for analysis and evaluation of schlieren.

The method for analysis or evaluation of schlieren according to the invention comprises the steps of:

a) irradiating a test sample with light from a light source;

b) producing a shadow image of the test sample on a projection screen;

c) receiving the shadow image of the test sample projected on the projection screen in an electronic image receiving device, preferably a digital camera;

d) processing the shadow image of the test sample received in the electronic image receiving device to measure the image contrast of the schlieren of the test sample; and e) comparing the measured image contrast of the shadow image of the test sample with the image contrasts of a shadow image of the schlieren of a comparison sample and analyzing or evaluating the schlieren of the test sample according to the comparison results.

The apparatus for performing this method according to the invention includes the light source for irradiating the test sample, a sample holder for holding the test sample or the comparison sample, a projection screen and of course the electronic image receiving device, preferably a digital camera.

According to the invention the shadow formed by the schlieren in a sample is acquired or received with the help of the digital camera and the contrast of the shadow image is determined by image processing. Since a direct measurement of the wave front delay in the material by changing the optical wavelength is not possible with shadow methods, the image obtained with the shadow methods is standardized or calibrated by means of structures with known wave front delays. The schlieren of an arbitrary sample (comparison sample) is measured interferometrically and correlated with the shadow image or contrast of the respective schlieren. In this way a simple shadow contrast to be measured may be correlated to the interferometrically measured schlieren type. This correlation is also designated the primary or original calibration. As comparison sample preferably pieces of a crystal are used, which comprise the same material as te optical material of the test sample to be evaluated. Test samples are especially preferred, which have different schlieren patterns, such as strong schlieren or weak schlieren.

In other words, the shadow methods may be used in practice to determine the optical quality of materials, especially crystalline materials, by the calibration performed by connecting the values obtained with the shadow methods with interferometrically obtained values.

The present invention thus is based essentially on shadow methods in combination with a new comparison process in which the comparison does not occur visually, but by means of electronic image formation.

The schlieren pattern received by the camera is processed digitally and the obtained digital image is compared with the schlieren pattern from the original or primary calibration, so that the average wave front deviation can be accurately determined with interferometric precision. Detection limits of less than 5 nm phase shift are possible at a wavelength of about 550 nm without more. A digital CCD camera can be used as the electronic image processing device according to the invention. The required resolution of the camera for the image processing however depends on the respective materials to be tested, also on the interferometer. Preferably it amounts to at least 10 micron/pixel, preferably at least 15 microns/pixel. For example, 20 microns/pixel are attained with calcium fluoride.

The samples to be evaluated by the method according to the invention and the apparatus according to the invention do not require expensive interferometric measurements. An interferometric calibration of the measuring arrangement for shadow images of the comparison sample made of the same material is required only once. In this calibration the calibration values obtained by it can be compared later to the values obtained from the test sample, since it has been shown that the product of the phase shift squared times the phase width always leads to the same contrast. Preferably the calibration values of the original or primary calibration are stored directly in the processor or processing means, so that the calibration data (virtual schlieren plate) arises, which can be retrieved at any time.

According to the invention the calibration values of the original or primary calibration are still compared with the shadow cast by a conventional synthetic schlieren plate. Since the contrast or the established contrast with the camera also depends on the screen, on which the shadow is produced, and on the focusing and brightness of the light source, it is possible in a simple manner to test whether the calibration is always still valid by means of a synthetic schlieren plate.

The electronic image processing of the test sample shadow image and the comparison sample image permits a quantitative classification of the occurring schlieren, which does not depend on subjective decisions of an observer. The determination of the schlieren by means of shadow formation in this way is fast, simple and economical.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which.

DETAILED DESCRIPTION OF THE INVENTION

The measurement process according to the shadow method described in the following detects and evaluates schlieren with interferometric precision in glassy and crystalline optial materials in the sense of an RMS wave front deformation $w_{rms}$. To classify the sample the value $w_{rms}^2$ is derived, which is proportional to the sum of the square of phase shifts times the widths and times the lengths of the respective individual schlieren, summed over all schlieren, the sum being divided by the total surface area of the sample, i.e. the value $w_{rms}^2$ and which is given by formula (1):

$$w_{rms}^2 = (\kappa/F)\Sigma LBw^2 \quad (1),$$

wherein $\kappa$=proportionality factor;
F=total area of sample,
w=a phase shift,
L=length of the schlieren (in the material),
B=width of the schlieren (in the material).

The image contrast $\Delta T$, which a given optical system provides, is connected with the RMS wave front deformation $w_{rms}$ at a given wavelength $\lambda$ by the following relationship in the form of formula (2):

$$\Delta T = ((4\pi/\lambda)w_{rms})^2 \quad (2):$$

Schlieren is required to be detected and evaluated, for example, at a wavelength of 550 nm with phase shifts of 5 nm or less, especially in crystals used in the UV spectral range.

The measurement process is designed so that it is suitable for continuous testing of a production process. Especially an optical material can be tested in the production process without additional finishing disregarding the required polishing. In order to detect and evaluate the schlieren the sample of the optical material to be tested may be rotated and tipped.

An apparatus for detection and evaluation of schlieren is described in the following paragraphs.

Figure 1:
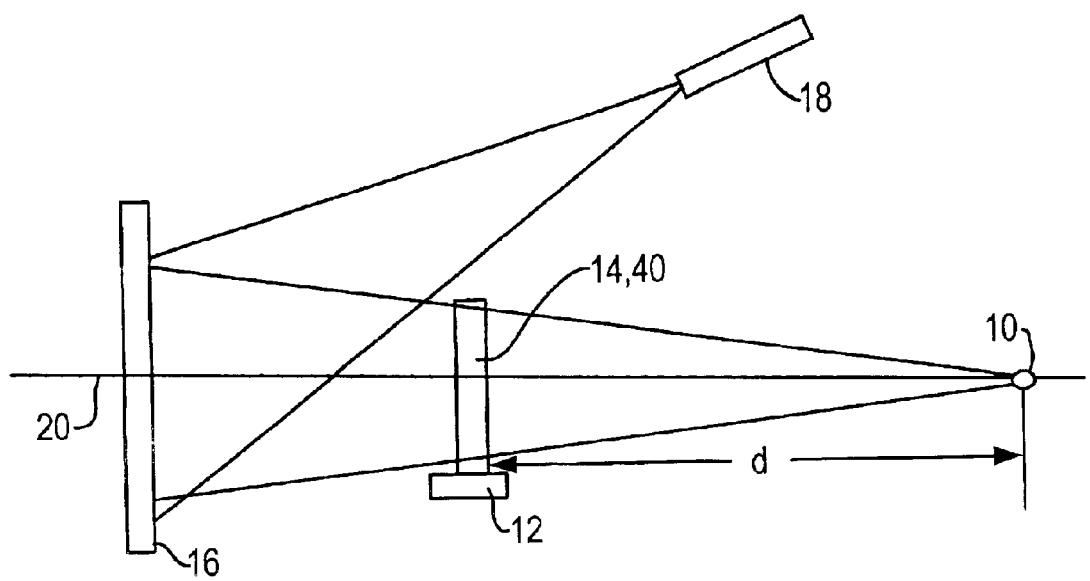
FIG. 1 is schematic cross-sectional view through an apparatus for measurement of schlieren of a test sample by the shadow method according to the invention.

The apparatus substantially comprises the optical device shown in FIG. 1 with a point light source 10, a sample holder 12, a test sample 14 to be tested, a projection screen 16 and a preferably digital camera 18. Although in the simplified embodiment described in FIG. 1 divergent light is used, the method and apparatus of the invention also operate with parallel light. In the measurement process a comparison sample 40 is also arranged in the sample holder 12. The phase shift pattern measured interferometrically from the schlieren of known phase shift and known width of a comparison sample is used for calibration of the shadow image and for comparison with the shadow image of the test sample 14. A synthetic schlieren plate can be used in place of the comparison sample 40. The synthetic schlieren plate includes preferably raised elements or surface portions (bumps) with a positive phase shift in stages of about 5 nm to about 50 nm and widths of about 0.1 mm to about 0.5 mm at a wavelength of, for example, 550 nm. The substrate material and the raised elements or surface portions (synthetic or artificial schlieren) are made from stable material with the same index of refraction as the bulk material.

Since the phase shift in the comparison sample 40 also depends on the material, comparison samples which are made of the same material as the test sample 14 are used. Alternatively it is always possible to use other comparison samples made of different material and to calibrate them with a comparison sample made from the same optical material as the sample that is tested. The schlieren pattern of a calibrated schlieren plate calibrated in this manner can be correlated at any time to the schlieren pattern of a plate or a sample of another material, such as calcium fluoride or sodium fluoride.

Quartz or quartz glass is preferably used for the schlieren plate, since it is an insensitive material.

In the calibration the shadow formation and thus the contrast to the synthetic schlieren plate is determined and subsequently or before that the phase shifts and phase widths of the respective shadow image of the test sample are measured by means of interferometry. Since the square of the phase shifts multiplied with the schlieren widths is proportional to contrast, in this way the contrast may be correlated with the product comprising the phase shifts and widths. The spatial resolution of the interferometer required depends on the schlieren widths to be measured. For example, for schlieren with a width of 0.1 mm a spatial resolution of 0.01 mm/pixel has proven sufficient. Preferably the spatial resolution per pixel is at least 5%, preferably at least 8% and especially preferably at least 10% of the schlieren width per pixel. In many cases an interferometer with a spatial resolution of 200 nm per pixel or less are used in the method.

The rms values to be measured may then be determined by the sum of the respective products, each of which is a square of the respective individual phase shift times the width and times the length of the individual schlieren, the sum being divided by the total surface area of the sample.

Of course in the method it is not possible to determine the phase shift or the width of a schlieren independently from the shadow image. However specification of the optical material is not required. The correlation between contrast and rms value is only slightly dependent on the width of the schlieren, which is thus sufficient for a definite schlieren classification.

The schlieren should be measured at the same incidence angle that is used in the application of the materials measured. The same is true of the angle of emergence.

The visibility of the schlieren in the test sample depends on the angle of incidence. A change of the incidence angle of the light of about one or two degrees can lead already to disappearance or conspicuous changes in the shadow image.

The light source 10, the test sample 14 and the projection screen 16 are arranged along the optic axis 20 of the measurement apparatus. The optic axis 20 extends through the light source 10 and the central point of the sample 14. The projection screen 16 is perpendicular to the optic axis 20. The distance d between the light source 10 and the sample 14 amounts to about 2 m and the distance between the test sample 14 and the projection screen 16 is about 1 m.

The camera 18 is arranged somewhat laterally or to the side of the optic axis 20, so that the shadow image of the test sample 14 on the projection screen 16 can be received without the test sample 14 or another element of the apparatus blocking or extending into the image field of the camera 18. So that the perspective deformation remains small, the angle between the optic axis 20 of the measurement apparatus and the optic axis of the camera 18 is kept as small as possible. Also the projection screen 16 can be inclined to the camera 18 according to choice or arbitrarily.

The sample holder 12 receives the usually disk-shaped sample 14 made of glassy or crystalline optical material. The sample 14 is gripped in the sample holder 12 so that the surfaces of the sample 14, through which the optic axis 20 of the measurement apparatus extends, extend perpendicular to this optic axis. The optical center point of the sample 14 is located always on the optic axis 20 of the measurement apparatus. The sample 14 can be tilted about ±50 degrees about a perpendicular tilting axis, which intersects the optical axis 20 at a right angle. Furthermore the sample 14 can be rotated around its center point at least about 90 degrees about a rotation axis intersecting the optic axis 20.

The surfaces of the test sample 14, through which the optical axis 20 extends, are parallel to each other and polished in the manner usual for optical elements.

The pattern of the synthetic schlieren plate 40 serves for comparison of the schlieren image of the test sample 14 obtained with the shadow methods with schlieren of known phase shift and known width.

The shadows of the schlieren of the test sample 14 or the synthetic schlieren plate 40 are projected on the projection screen 16 in the measurement apparatus. The sample 14 in the sample holder 12 is illuminated with a predetermined light cone by a point source 10 of high illumination power. The illumination intensity on the projection screen 16 similarly amounts to preferably at least 100 lux. The light cone is preferably formed as a divergent light beam. Additional optional optical elements, such as a UV blocking filter, may be arranged in the light path only in the immediate vicinity of the light source or contingent real image.

After the light beam passes through the sample the shadow image arises as a phase dependent superposition of the light detracted by the schlieren with the primary light cone from the light source. The schlieren information is primarily contained in the first approximately in the phases, whereby only a small component is amplitude modulated and only this portion is detected without further effort as an intensity difference.

This very contrast-poor amplitude image is now received as interference-free as possible with a high signal-to-noise ratio. Moreover it is advantageous to detect the actual image produced on the projection screen 16, not an image produced in the air with the help of optics. The projection screen 16 must provide diffuse light scattering without light-directly elements and must have no detectable surface structure. The diffuse reflectivity may not vary from place to place on the screen.

Since the screen image has less than 1% contrast, it is necessary to amplified the contrast already in the digital camera 18 so that a subsequent digitization can take place in order to store the image in digital form in a data bank. Furthermore for this purpose a CCD camera with the highest possible pixel count (for example 1300×1030 pixels) and at least one 12 bit digitization means must be used.

The raw data received with the camera must be processed in order to eliminate local sensitivity differences of the camera 18 and contingent local variations on the projection screen 16. It also must be processed to obtain a representation of the schlieren with high contrast, which is possible by means of conventional computer programs, like that which is obtained by means of image processing software with contrast and intensity control or detection together with commercial/CCD cameras.

Figure 3:
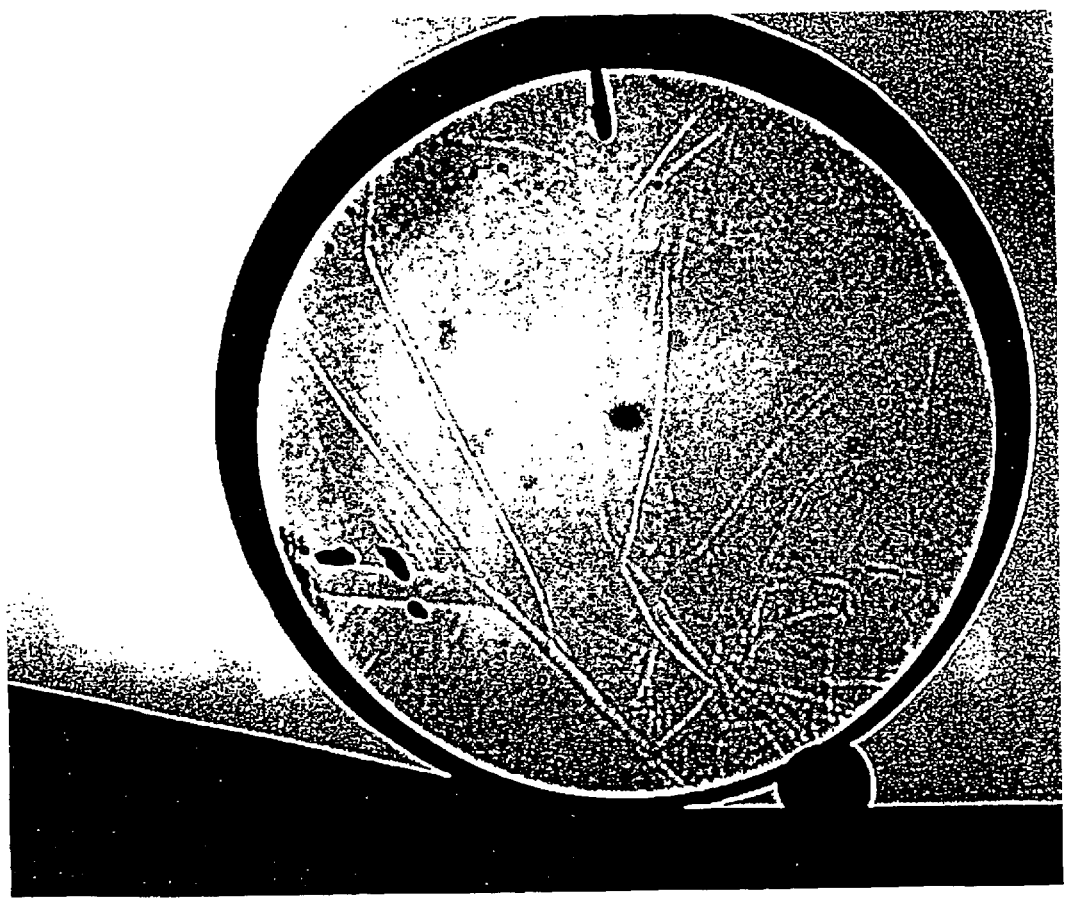
FIG. 3 is a plan view of a typical schlieren pattern in an optical crystal.

The processing of the raw data takes places simply and easily by software, which must be prepared. The schlieren image detection should be able to distinguish between scratches, naps, surface defects and poor cleaning of the of the disk/optics. Also schlieren that are smaller than the noise can be detected with suitable contrast. Principally the image detection is a copy of the cooperation of the eye and the brain, which means that the schlieren are distinguished as in the case of human detection, by means of contrast variations. Accordingly a schlieren filter searches along a line for points or regions with average, dark or bright light intensity. As shown in FIG. 3, a schlieren is characterized by an elongated shape with a bright central region and dark edges. In contrast a schlieren-free region is characterized by an average brightness. A cross-section through a region, which contains schlieren, thus shows a transition from average brightness (schlieren-free region) to dark schlieren edge, then to bright schlieren center and again to dark schlieren edge opposite the first schlieren edge and finally to average brightness. When neighboring regions that follow each other in a longitudinal direction have this sort of brightness signature, it can be concluded that a schlieren has been detected. This sort of software can be optimized in a known manner by means of a plurality of known parameters. That means that the contrast thresholds between average-dark-bright-dark-average signatures must be set up and the symmetry of the brightness signatures must be established. Moreover the number of neighbors having the same signature that establishes the presence of a schlieren structure must be determined. Similarly the widths of these type of schlieren varies. A typical schlieren image is shown in FIG. 3.

To control the reception conditions, for calibration and for correlation of the image contrast of schlieren from a test sample 14 of the optical material to be tested with schlieren of a predetermined widths and phase shifts the artificial schlieren plate 40 is put in the sample holder 12. The image of the schlieren pattern on the projection screen 16 is received in the camera 18. Then the dependence of the schlieren contrast on the phase shift is measured for the same image scale, offset and magnification or amplification of the camera.

Figure 2:
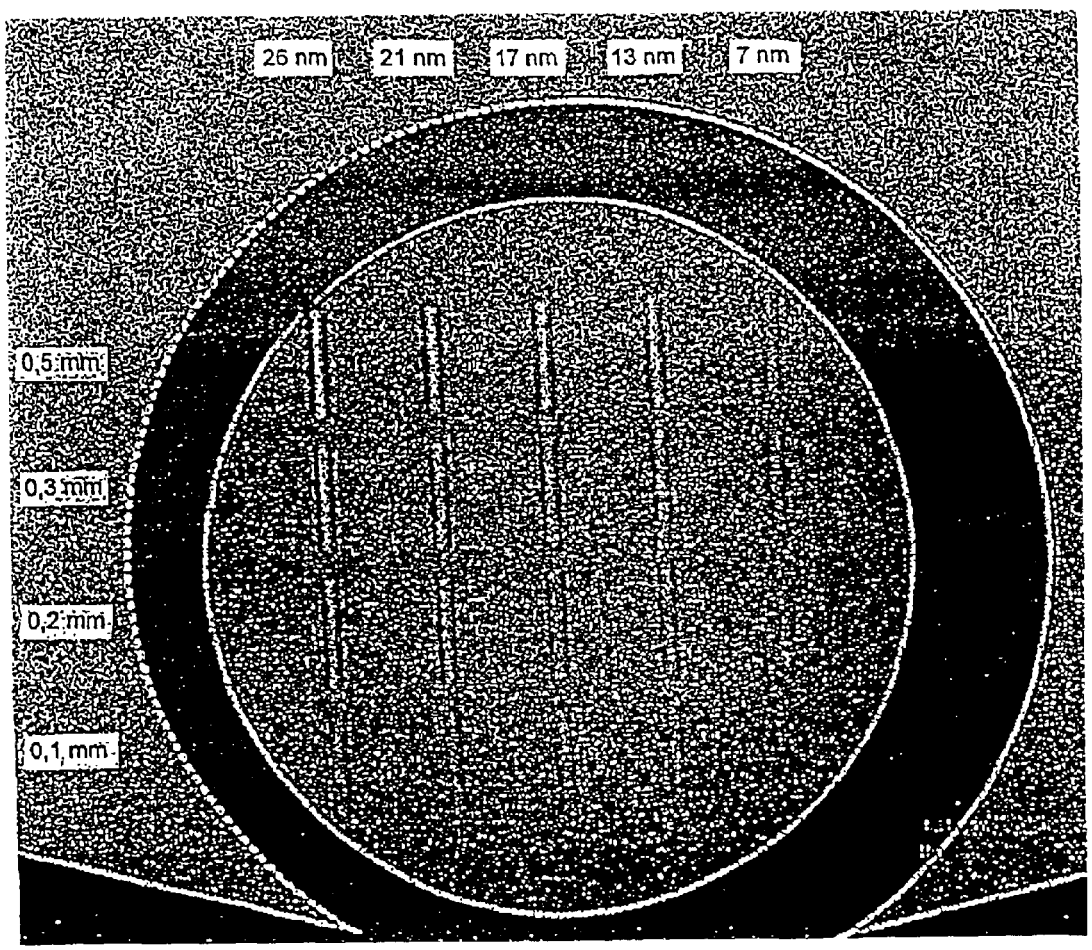
FIG. 2 is a plan view of a shadow image of a synthetic schlieren plate comprising a comparison sample with artificial schlieren according to the invention.

FIG. 2 shows the shadow image of an artificial schlieren plate 40 obtained with the above-described measurement apparatus. FIG. 2 also includes the numerical values of the phase shifts and schlieren widths. The image contrast measured on the synthetic schlieren plate 40 may be represented as a function of the phase shifts and the schlieren widths and compared with the image contrast of the test sample 14 made from the material to be tested.

The comparison occurs in an electronic image processing device connected to the camera 18. The gray scale values for the measured image contrasts are compared with each other and a quantitative evaluation of the schlieren in the test sample 14 is derived from that comparison.

It is not necessary to take a new shadow image of the artificial schlieren plate 40 for the same type of test sample 14. The shadow image of the artificial schlieren plate 40 can be stored electronically in the image processing device in an already more or less prepared form.

The calibration with the synthetic schlieren plate 40 is thus in principle only required once, since all further comparisons can be performed in the computer or processing means. The reason is because the image intensities or contrasts produced with the artificial schlieren plate are stored in the computer or processing means as the basis for the comparison. In spite of that it can be important from time to time to test whether the contrast values or intensities of the image obtained by the camera with the artificial schlieren plate have changed. The reason for that can be, for example, a change in the camera focusing, dust and dirt on the lens of the camera or also an engineering defect. The same goes of course for the light source, with which the schlieren is produced. Aging of the light source, the lens and the other components can also cause such changes in the illumination intensities. In later measurement the artificial schlieren plate 40 is exclusively adjusted to guarantee that the reference values stored in the computer or processing means always are valid.

The above-described process and the above-described apparatus are suitable not only for determination of schlieren in materials for artificial lenses, but also in materials for other optical elements, for example prisms, cubes, light guides and the like. Use of calcium fluoride, barium fluoride, strontium fluoride and sodium fluoride crystals, as well as other crystals, especially large-sized crystals, is especially preferred.

The invention of course also concerns the use of the apparatus and method according to the invention for testing materials used to manufacture lenses, prisms, light guide rods, optical windows and other optical components, such as those for DUV photolithography, steppers, lasers, especially excimer lasers, wafers, computer chips, as well as integrated circuits and electronic devices, which have circuitry and chips.

The disclosure in German Patent Application 101 11 450.8 of Mar. 9, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method and apparatus for analysis of schlieren, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of analysis of schlieren, said method comprising the steps of:
    a) irradiating a test sample with light from a light source;
    b) producing a shadow image of the test sample on a projection screen;
    c) receiving the shadow image of the test sample projected on the projection screen in an electronic image receiving device;
    d) processing the shadow image received in the electronic image receiving device to measure schlieren image contrast; and
    e) comparing said schlieren image contrast measured in the shadow image of the test sample with schlieren image contrast of a shadow image of a schlieren pattern of a comparison sample and evaluating the schlieren of the test sample by means of the comparing.

2. The method as defined in claim 1, wherein said schlieren pattern of said comparison sample is measured interferometrically to obtain interferometric measurements and further comprising calibrating said schlieren image contrast of the test sample with said interferometric measurements.

3. The method as defined in claim 2, wherein the comparison sample and the test sample are made from identical optical materials.

4. The method as defined in claim 1, wherein the comparison sample is made from a different material than that of the test sample and the comparison sample made from said different material is calibrated with another comparison sample made of another material that is identical to said optical material of the test sample.

5. The method as defined in claim 1, further comprising calibrating a synthetic schlieren plate comprising said comparison sample, which has an artificial schlieren with a positive phase shift in stages of about 5 nm to about 50 nm and widths of about 0.1 mm to about 0.5 mm at a wavelength of 550 nm.

6. The method as defined in claim 1, further comprising tilting and rotating said test sample in a plurality of directions in relation to an optical axis of a measurement device for the processing of the shadow image.

7. The method as defined in claim 3, wherein said optical materials each comprise a crystalline or a glassy material.

8. The method as defined in claim 4, wherein said different material and said optical material each comprise crystalline or glassy material.

9. The method as defined in claim 3 or 4, wherein said optical materials each or said different material consists of crystalline material and said crystalline material is calcium fluoride or barium fluoride.

10. The method as defined in claim 1, wherein the electronic image receiving device is a digital camera.

11. An apparatus of analysis of schlieren, said apparatus comprising:
    means for irradiating a test sample with light from a light source, said means for irradiating including a sample holder and the light source;
    means for producing a shadow image of the test sample on a projection screen, said means for producing the shadow image including the projection screen;
    means for receiving the shadow image of the test sample projected on the projection screen in an electronic image receiving device;
    means for processing the shadow image received in the electronic image receiving device to measure schlieren image contrast, said means for processing the shadow image being connected electronically with said means for receiving the shadow image;
    means for comparing the measured schlieren image contrast measured in the shadow image of the test sample with schlieren image contrast of a shadow image of a schlieren pattern of a comparison sample and evaluating the schlieren of the test sample by means of the comparing.

12. The apparatus as defined in claim 11, wherein the shadow image of the comparison sample or a synthetic schlieren plate comprising the comparison sample is stored in the electronic image processing device.

13. The apparatus as defined in claim 11, wherein the electronic image receiving device comprises a digital camera.

14. A process for evaluating an optical material for the manufacture of lenses, prisms, light conductive rods, optical windows and optical components for DUV photolithography, steppers, lasers including Excimer lasers, wafers, computer chips, integrated circuits and electronic devices including integrated circuits, said process comprising a method of analysis of schlieren of said optical material, said method comprising the steps of:
    a) irradiating a test sample of said optical material with light from a light source;
    b) producing a shadow image of the test sample on a projection screen;
    c) receiving the shadow image of the test sample projected on the projection screen in an electronic image receiving device;
    d) processing the shadow image received in the electronic image receiving device to measure schlieren image contrast; and
    e) comparing the measured schlieren image contrast measured in the shadow image of the test sample with schlieren image contrast of a shadow image of a schlieren pattern of a comparison sample and evaluating the schlieren of the test sample by means of the comparing.

15. The process as defined in claim 14, wherein the electronic image receiving device is a digital camera.

16. The process as defined in claim 14, wherein the comparison sample is made from a different material than that of the test sample and the comparison sample made from said different material is calibrated with another comparison sample made of another material that is identical to that of the test sample.

* * * * *